(12) United States Patent
Krueger (10) Patent No.: US 9,474,813 B2
(45) Date of Patent: Oct. 25, 2016

(54) APPARATUS AND METHOD FOR STERILIZING CONTAINERS WITH X-RAY RADIATION MONITORING

(71) Applicant: KRONES AG, Neutraubling (DE)

(72) Inventor: Jochen Krueger, Hagelstadt (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 14/647,719

(22) PCT Filed: Nov. 27, 2013

(86) PCT No.: PCT/EP2013/074857
§ 371 (c)(1),
(2) Date: May 27, 2015

(87) PCT Pub. No.: WO2014/083054
PCT Pub. Date: Jun. 5, 2014

(65) Prior Publication Data
US 2015/0297765 A1 Oct. 22, 2015

(30) Foreign Application Priority Data
Nov. 27, 2012 (DE) .......................... 10 2012 111 494

(51) Int. Cl.
*A61L 2/00* (2006.01)
*A61N 5/00* (2006.01)
(Continued)

(52) U.S. Cl.
CPC ................ *A61L 2/087* (2013.01); *B65B 55/08* (2013.01); *A61L 2202/14* (2013.01); *A61L 2202/23* (2013.01)

(58) Field of Classification Search
CPC .............. A61L 2/00; A61L 9/18; A61L 9/20
USPC ................................ 422/1, 21–22; 250/492.3
See application file for complete search history.

(56) References Cited

U.S. PATENT DOCUMENTS

| | | | |
|---|---|---|---|
| 4,887,604 A | 12/1989 | Shefer et al. | 128/654 |
| 5,635,714 A | 6/1997 | Nablo et al. | 250/305 |
| 6,914,253 B2 | 7/2005 | Korenev et al. | 250/492.3 |

(Continued)

FOREIGN PATENT DOCUMENTS

| | | | | |
|---|---|---|---|---|
| DE | 102011056628 | 6/2013 | | A61L 2/08 |
| EP | 2316495 | 5/2011 | | A61L 2/08 |

(Continued)

OTHER PUBLICATIONS

German Search Report (no translation) issued in application No. 10 2012 111 494.3, dated Oct. 9, 2013 (5 pgs).

(Continued)

*Primary Examiner* — Monzer R Chorbaji
(74) *Attorney, Agent, or Firm* — Hayes Soloway P.C.

(57) ABSTRACT

An apparatus for sterilizing containers includes a transport device which transports the containers along a predefined transport path (P), a radiation device which applies radiation (S) to at least some sections of the containers and/or components of the apparatus for sterilization purposes, and a sensor device which detects radiation occurring as a result of the radiation (S) emitted by the radiation device. The apparatus has a shielding element which attenuates the radiation reaching the sensor device in a working mode of the apparatus, and a movement device for moving said shielding element relative to the sensor device.

21 Claims, 3 Drawing Sheets

(51) Int. Cl.
 *A61L 2/08* (2006.01)
 *B65B 55/08* (2006.01)

(56) References Cited

U.S. PATENT DOCUMENTS

| | | | |
|---|---|---|---|
| 8,415,633 B2 | 4/2013 | Keil et al. | 250/370.01 |
| 8,461,550 B2 | 6/2013 | Nishino et al. | 250/455.11 |
| 2012/0145929 A1* | 6/2012 | Nishino | A61L 2/087 250/492.3 |
| 2014/0369885 A1 | 12/2014 | Krueger | 422/22 |

FOREIGN PATENT DOCUMENTS

| | | | | |
|---|---|---|---|---|
| EP | 2462953 | 6/2012 | | A61L 2/08 |
| WO | WO 2006108453 | 10/2006 | | A61L 2/08 |
| WO | WO 2010121775 | 10/2010 | | A61L 2/08 |
| WO | WO 2013092735 | 6/2013 | | A61L 2/08 |

OTHER PUBLICATIONS

International Search Report (no translation) issued in application No. PCT/EP2013/074857, dated Jan. 28, 2014 (11 pgs).

* cited by examiner

APPARATUS AND METHOD FOR STERILIZING CONTAINERS WITH X-RAY RADIATION MONITORING

BACKGROUND OF THE INVENTION

The present invention relates to an apparatus and a method for sterilizing containers and in particular plastic containers. It is known from the prior art that containers are sterilized prior to being filled, particularly when being filled with certain sensitive beverages. Various procedures are known for the purpose of this sterilization, such as, for example, applying a sterilizing medium such as peracetic acid or hydrogen peroxide. More recently, however, efforts have been made to reduce the use of such chemicals.

In general, however, the sterilization of containers is, besides the actual filling operation, the main process step in a, particularly aseptic, bottling system, wherein hereinbelow containers will be understood to mean both finished containers, such as plastic containers or glass bottles, and for instance plastic preforms which are to be expanded into bottles. When disinfecting the containers by means of beams, particularly electron beams, firstly the reliability of the treatment, i.e. the sterilizing effect on each individual container, is important. Another important criterion, however, is also the safety of the operators and staff on the system, particularly since undesired side effects, such as X-ray radiation, occur when applying, for example, electron beams.

As mentioned, when irradiating the containers with high-energy electrons, X-ray radiation also occurs as an undesired side effect. In order to protect the staff and also electronic components in the environs of the machine against this radiation, usually shields are fitted which are made of a material having a sufficient wall thickness. For electron beams having an energy in the region of 150 keV, lead walls having a thickness of 5-12 mm are required for shielding the X-ray radiation (this also depends on the current). As an alternative, a different material can also be used, such as steel for example, but the shielding effect of steel is much lower and therefore the wall thickness must accordingly be thicker.

In any case, the entire system is shielded such that, for the defined radiation parameters and when the system is used as intended, i.e. during normal operation, a residual radiation of more than 1 μSv/h cannot occur at any point outside the system. However, a malfunction may also occur if, for example, one or more of the emitters is defective or is controlled incorrectly, so that increased radiation is produced. In order to ensure this intended or "normal" operation, use is made of detectors and/or sensor devices. A monitoring of this radiation by means of X-ray detectors is known from the internal prior art.

These sensor devices or radiation detectors have to function reliably over many operating hours since they ultimately monitor the radiation safety of the machine and if necessary trigger an emergency stop. During normal operation, the scenario of excess radiation generally does not occur, so that the sensors detect no malfunction and do not trigger an emergency stop for days, weeks or months. It is therefore necessary to check the functioning of the sensor devices at regular time intervals. Several possible ways of doing this are known from the prior art.

In one procedure, the sensitivity of the sensor can be electronically increased, and/or the measurement signal thereof can be additionally amplified. The evaluation of the signal shows a radiation level that is supposedly too high, which must lead to the emitters being switched off. Another checking option lies in exposing the sensor to an increased radiation level so that it has to switch off the radiation sources where necessary, depending on its task. In the simple case, this could be achieved by increasing the normal radiation level inside the machine. However, this should be avoided for reasons of radiation safety. However, both of the aforementioned possibilities have the disadvantage that the system is manipulated and that safety-critical components of the machine are altered. The sensor, the sensor electronics and also the evaluation unit are part of a safety technology.

The object of the invention is therefore to enable such monitoring of the systems without to this end carrying out the manipulations, necessary in the prior art, on safety-critical components.

SUMMARY OF THE INVENTION

An apparatus according to the invention for sterilizing containers has a transport device which transports the containers along a predefined transport path. The apparatus also has a radiation device which applies radiation to at least some sections of the containers and/or components of the apparatus for sterilization purposes. Also provided is a sensor device which detects (in particular further) radiation occurring as a result of the radiation emitted by the radiation device.

According to the invention, the apparatus has a shielding element which attenuates the radiation reaching the sensor device in a working mode of the apparatus, and a movement device for moving said shielding element relative to the sensor device and/or for generating a relative movement between the sensor device and the shielding element.

It is therefore proposed according to the invention to increase the radiation level to which the sensor device is exposed during normal operation, without manipulating the measuring or emitter system. The possibility lies in attenuating, by means of a shielding element, the radiation reaching the sensor device during normal operation. As a result, the sensor device experiences a permanently weaker radiation signal than is actually present in the machine.

In order to test the sensor device, the shielding element is preferably pulled away from the sensor device and the sensor device then detects a much stronger X-ray signal, even though the radiation level in the machine is unchanged (and also safe) and also the sensor device itself has not been altered. As a result, the sensor device should then trigger an alarm and initiate switch-off of the radiation sources.

However, it would also be possible to move not the shielding element but rather the sensor device, for instance to move the sensor device out of a shadow thrown by the shielding element, which can take place for example by a linear movement and/or a pivoting movement of the sensor device.

Preferably, the radiation to be detected by the sensor device is X-ray radiation. X-ray radiation is considerably attenuated as it passes through matter. The radiation interacts with the matter through which it passes and the energy of the photons is absorbed in the material due to the photoelectric effect and Compton scattering. The intensity of the radiation passing through decreases exponentially with the distance travelled in the material, according to the Beer-Lambert law ($I=I_0 x e^{-kx}$). Here, the mass attenuation coefficient k depends on the material that is penetrated and the wavelength of the radiation. Numerous tables for such attenuation coefficients are known in the prior art. However, it would also be possible that X-ray radiation is used directly to sterilize the containers. Within the context of this disclosure, sterilization is understood to mean a process which serves to reduce the number of viable microorganisms at least to a certain extent.

For example, it can be calculated that a sheet of iron having a thickness of 2 mm attenuates by approximately 50% the intensity of an X-ray radiation that has been generated by electrons with an acceleration voltage of 90 kV.

More specifically, for example, the X-ray radiation produced with electrons accelerated at an acceleration voltage of 90 kV is attenuated by 32% by a sheet of iron having a thickness of 1 mm, by 53% by a sheet of iron having a thickness of 2 mm, by 68% by a sheet of iron having a thickness of 3 mm, by 78% by a sheet of iron having a thickness of 4 mm and by 85% by a sheet of iron having a thickness of 5 mm. At an acceleration voltage of 125 kV, the attenuation is 18% with a sheet of iron having a thickness of 1 mm, 33% with a sheet of iron having a thickness of 2 mm, 45% with a sheet of iron having a thickness of 3 mm, 55% with a sheet of iron having a thickness of 4 mm and 63% with a sheet of iron having a thickness of 5 mm. These values can also be confirmed by experiments.

The radiation device is preferably a radiation device which is arranged in a stationary manner and past which the containers move. In this case, the radiation device serves in particular to irradiate the outer surfaces of the containers. However, it would also be possible that the radiation device serves for treating the inside of the containers and has, for example, a rod-shaped body or emitting finger which is introduced into the interior of the containers. In this case, these radiation devices or emitting fingers are preferably moved with the containers.

In another advantageous embodiment, the apparatus has both radiation devices for treating the outside of the containers and radiation devices for treating the inside of the containers. However, the radiation device may also serve to sterilize elements of the apparatus, for instance gripping clamps which hold the containers during the sterilization thereof or also other regions of the sterilizing device such as, for example, housing walls or the like. A plurality of such sterilizing devices can also be used for different purposes.

Preferably, the apparatus has a clean chamber, inside which the containers are transported during their sterilization. Advantageously, this clean chamber is delimited from a surrounding environment (which in particular is unsterile) by means of at least one wall. Sealing devices may also be provided, which seal off the clean chamber or walls of the clean chamber which are movable relative to one another. For this, consideration may be given, for example, to a so-called water lock which comprises a peripheral, liquid-filled channel into which there dips a blade (which in particular is able to rotate) that is connected to the respective other wall.

In a further advantageous embodiment, the transport device for transporting the containers has a carrier wheel, on which there is arranged a plurality of holding devices for holding the containers. In this embodiment, the containers are preferably guided along a circular transport path during their sterilization.

In a further advantageous embodiment, the containers to be sterilized are plastic preforms or plastic bottles.

In a further advantageous embodiment, the movement device is configured in such a way that it can remove the shielding element at least partially from a beam path of the radiation reaching the sensor device. In other words, the sensor device or a detector element can be covered by the shielding element during normal operation of the system and the shielding element may be removed only for test purposes.

In this case, it is preferably also possible that the shielding element is removed during ongoing operation, or in general said relative movement between the shielding element and the sensor device is carried out during ongoing operation. In this way, it is possible in particular to check the radiation device and/or the sensor device during ongoing operation.

Advantageously, the movement device is configured in such a way that the shielding element can be removed from the beam path within a predefined time period which is less than 200 ms, preferably less than 100 ms, preferably less than 50 ms and particularly preferably less than 30 ms. Advantageously, such a measurement within the working mode, i.e. in particular including the removal of the shielding element, the actual measurement and the subsequent reintroduction of the shielding element, is possible within a time period that is shorter than 200 ms, preferably shorter than 100 ms, preferably shorter than 50 ms, preferably shorter than 30 ms and which is preferably in a range between 20 ms and 30 ms.

In this case, preferably a control device is also provided which, during the checking of the sensor device, also takes account of a position of the containers to be sterilized. Preferably, the control device is provided such that the respective checks are always carried out at a same location of the containers, i.e. always when the containers are located at a predefined and constant position relative to the sensor device. In this way, a comparability of multiple checking measurements can be ensured.

Advantageously, the apparatus also has a memory device in which measured values of such checking measurements can be stored. In this way, it is possible to carry out long-term measurements and to record a long-term log.

However, it would also be possible that the checking measurements are carried out at different container positions. With this procedure, however, the respective position of the containers to be sterilized is also detected. The apparatus therefore preferably also has a detection device which detects a relative position of the containers during the checking of the sensor device.

In a further advantageous embodiment, the radiation device is an electron radiation device which emits electron beams. More specifically, these are accelerated electrons. Advantageously, therefore, the radiation device has an accelerating device for accelerating the electrons. Advantageously, the radiation device also has an exit window, through which the accelerated electrons can exit from a housing, inside which they are accelerated. This exit window is advantageously made of titanium. In a further advantageous embodiment, the exit window has a thickness of between 4 μm and 30 μm, preferably between 6 μm and 20 μm. Advantageously, the apparatus also has a cooling device for cooling this exit window.

In a further advantageous embodiment, the electrons are accelerated with an acceleration voltage of between 50 kV and 300 kV, preferably between 60 kV and 250 kV, preferably between 70 kV and 200 kV, preferably between 70 kV and 150 kV and particularly preferably between 80 kV and 150 kV. However, a sterilization by means of other charge carriers would also be conceivable, for instance by means of protons, alpha-particles and, the like.

In a further advantageous embodiment, the sensor device is suitable for and is intended for detecting X-rays. Advantageously, therefore, the radiation applied to the containers and the radiation to be detected by the sensor device differ from one another. However, the radiation to be detected by the sensor device is advantageously a result of the radiation by which the containers are sterilized. In particular, these are respectively braking radiation and X-ray radiation.

In a further advantageous embodiment, the shielding element attenuates the radiation impinging on the sensor device by at least 10%, preferably by at least 20%, preferably by at least 30%, and particularly preferably by at least 50%.

During normal operation, the radiation level inside the machine is high enough that even an attenuation by 30 to 50% still delivers very high measured values which are very easy to evaluate. On the other hand, however, the sensor device itself is not exposed during normal operation to the high loads occurring in the case of the (temporally very short) test mode.

Advantageously, the sensor device has a scintillator with a photomultiplier arranged particularly preferably downstream and particularly preferably also a counter tube. Alternatively, the sensor device may also have a counter tube or a semiconductor detector or a different detector which is suitable for detecting X-ray radiation quantitatively and with suitable precision.

In order to protect the electronics of the sensor device against permanent and excessive radiation exposure, the sensor device is advantageously accommodated in a radiation-proof housing which has walls having a wall thickness of several millimeters. Preferably, therefore, the sensor device has a housing which surrounds it. This housing may be designed for example as a lead casing. Advantageously, there is provided in this housing an opening which is at least partially and particularly preferably fully closed by the shielding element during normal operation. In a further advantageous embodiment, biasing means are also provided which urge the shielding element into a closed position. This means that the shielding element usually attenuates the radiation impinging on the sensor device.

The movement device can be any movement devices, such as, for example, electric drives, hydraulic drives, pneumatic drives and the like. A manual movement device would also be conceivable as the movement device, so that the user can for example manually move the shielding element out of the beam path impinging on the sensor device. For instance, the movement device may be, for example, a small slider which is integrated laterally into a bore in front of the sensor and which is temporarily removed from the bore by compressed air. In this case, after the test, a compression spring can push this slider back into its position in front of an aperture device, through which the radiation reaches the sensor device.

If the test is successful (which is expressed for example in that the system has been duly switched off), the attenuation sheet or the shielding element can be positioned back in the beam path and the machine can be put back into productive operation. If, despite the emitters being switched on, no automatic alarm is triggered in this test, this is a sign that the sensor device is not functioning as intended or that the aperture device has not been removed from the beam path (for example due to mechanical reasons). In this case, the system should likewise be switched off and a search for the fault should take place.

The present invention also relates to a method for sterilizing containers, wherein the containers are transported along a predefined transport path, and wherein the containers or components of the apparatus are sterilized at least in some sections by being exposed to radiation. In this case, further radiation occurring as a result of said radiation is detected by a sensor device.

According to the invention, a shielding element attenuates the radiation reaching the sensor device and this shielding element is moved at least at times (relative to the sensor device) such that the radiation reaching the sensor device is attenuated to a lesser degree. With regard to the method too, therefore, it is proposed that—particularly in a normal working mode, or sterilizing mode—the radiation reaching the sensor device is permanently attenuated. The shielding element is advantageously—particularly in the context of a test mode—moved such that the radiation reaching the sensor device is not attenuated or is attenuated to a lesser degree by this shielding element.

In other words, for checking purposes, particularly for checking the sensor device, the shielding element is moved such that the radiation reaching the sensor device is attenuated to a lesser degree. With regard to the method too, it would be possible that the relative movement between the sensor device and the shielding element is achieved by moving the sensor device.

The sensor device advantageously detects X-ray radiation. The sensor device advantageously outputs a signal which is characteristic of the X-ray radiation acting on the sensor device.

BRIEF DESCRIPTION OF THE DRAWINGS

Further advantages and embodiments will become apparent from the appended drawings, in which.

DETAILED DESCRIPTION OF THE INVENTION

Figure 1:
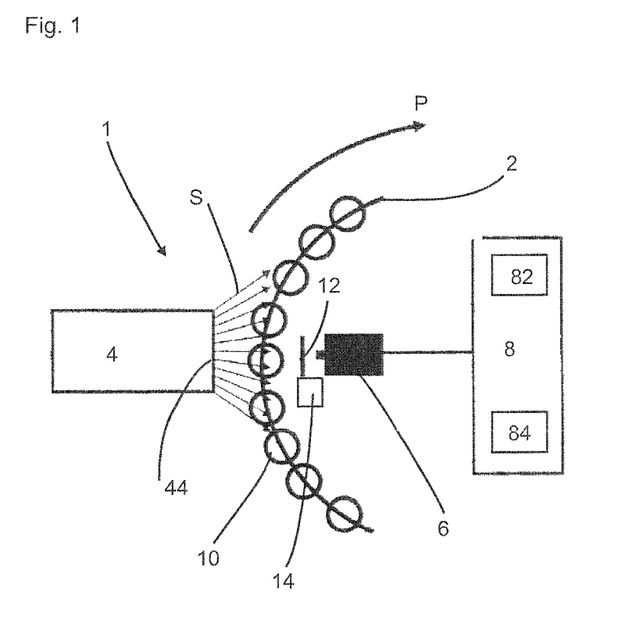
FIG. 1 shows a schematic diagram of an apparatus according to the invention in a first operating state.

FIG. 1 shows, in a first operating state, an apparatus 1 according to the invention for sterilizing containers 10. The containers 10, in this case plastic bottles or plastic preforms, are transported along a predefined transport path P by means of a transport device 2 which is shown only partially here and which is configured for example as a rotatable carrier. During transport, radiation S and in particular electrons are applied to the containers 10 by a radiation device 4 and in particular by an electron beam device 4. Said electrons exit from the device 4 via an exit window 44. In particular, the outer walls of the plastic containers are sterilized as a result of this irradiation.

Here, reference S denotes the radiation impinging on the containers. As a result of this irradiation of the containers, X-ray radiation also occurs (as a side effect) and is detected by a sensor device 6. Reference 8 denotes an evaluation device which evaluates the radiation impinging on the sensor device 6, for example with regard to the intensity thereof. This evaluation device 8 has a display device 82 which outputs to the user a signal or information that is characteristic of the detected X-ray radiation. Reference 84 denotes a comparison device which compares the radiation detected by the sensor device 6 with predefined reference values. Reference 12 denotes a shielding element which in a working mode here is arranged in front of the sensor device 6 or a sensor element of this sensor device 6 and thus attenuates the radiation detected by the sensor device 6.

Reference 14 denotes a movement device which serves to move the shielding element 12. It would also be possible to move not the shielding element 12 but rather the sensor device 6 out of the shadow of the shielding element to some extent. In any case, the shielding element 12 will no longer be arranged in the beam path impinging on the sensor device 6.

Figure 2:
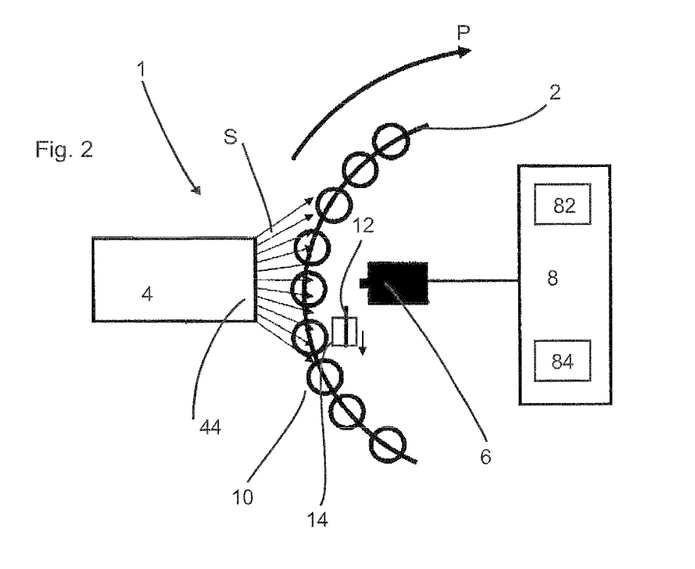
FIG. 2 shows the apparatus of FIG. 1 in a second operating state.

FIG. 2 shows the apparatus of FIG. 1, wherein now the shielding element 12 has been pushed aside and thus the beam path can impinge unhindered on the sensor device 6. Here, essentially any movements of this shielding element 12 are conceivable for removing it at least partially from the beam path.

Advantageously, this shielding element is a sheet of steel having a predefined thickness, as a result of which a suitably predefined shielding or attenuation of the X-ray radiation is also achieved. However, it would also be possible that this shielding element has a variable or changing thickness in order thus also to achieve different shielding effects. This would be relevant if the desire was not only to ascertain the quality of functioning of the sensor device but also about to check the functioning thereof in quantity terms. Conclusions for example about the state of ageing of the sensor device could also be drawn from such quantitative measurements.

Figure 3:
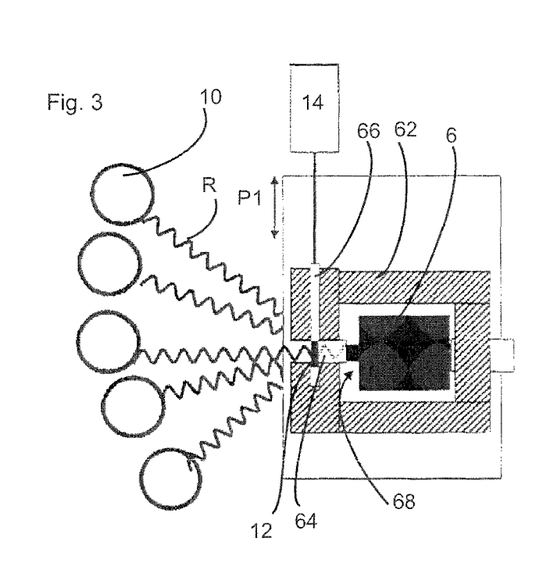
FIG. 3 shows a schematic diagram of a sensor device in a first operating state.

FIG. 3 shows an arrangement of a sensor device 6. This sensor device has a housing 62 which surrounds in particular the sensitive electronic components. Formed in this housing is an opening or aperture 64, through which X-ray radiation can reach the actual sensor element. Reference R denotes the (X-ray) radiation to be detected by the sensor device 6. Reference 68 thus denotes in a highly schematic manner a sensor element of the sensor device 6, on which the X-ray radiation impinges.

Here, reference 66 denotes a groove or a recess, within which the shielding element can slide or move. In the situation shown in FIG. 3, the shielding element is positioned in such a way that it covers the opening 64. A displacement of the shielding element is possible for example via compressed air, wherein, when the compressed air is switched off, the shielding element is in the position shown in FIG. 3.

Figure 4:
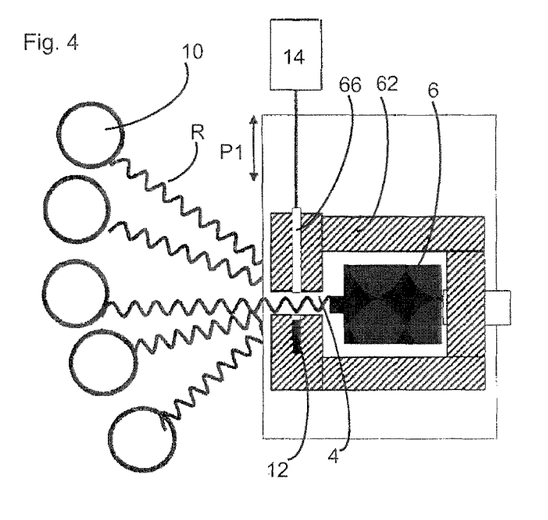
FIG. 4 shows the sensor device in a second operating state.

FIG. 4 shows the arrangement of FIG. 3, but here the shielding element 12 is displaced such that radiation can also pass through the opening 64 to the sensor device 6 without being attenuated by the shielding element 12. In this case, compressed air can be fed for example through the recess 66 in order to displace the shielding element 12.

Figure 5:
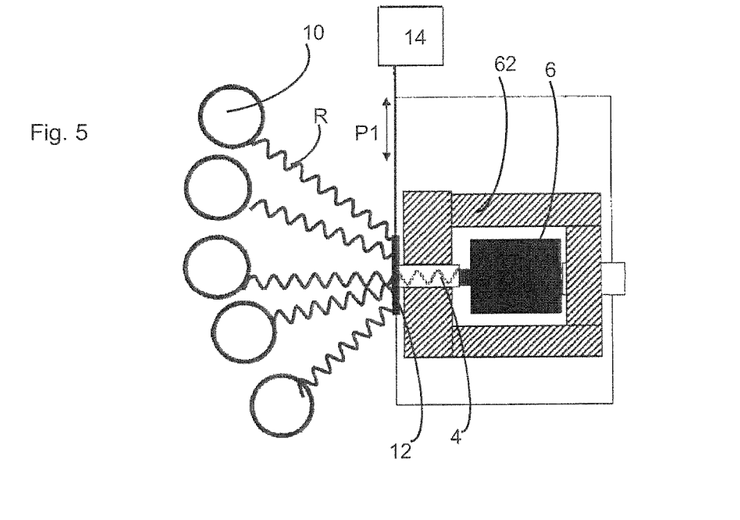
FIG. 5 shows a sensor device according to the invention in a second operating state.

FIG. 5 shows a further embodiment of a sensor device according to the invention. Here, the shielding element 12 is arranged on a lever which permits the displacement thereof in the direction of the double-headed arrow P1. In this way, too, the radiation can either pass unattenuated to the sensor device 6 or else is attenuated by the shielding element 12 when the latter is in a suitable different position.

Figures 6, 7:
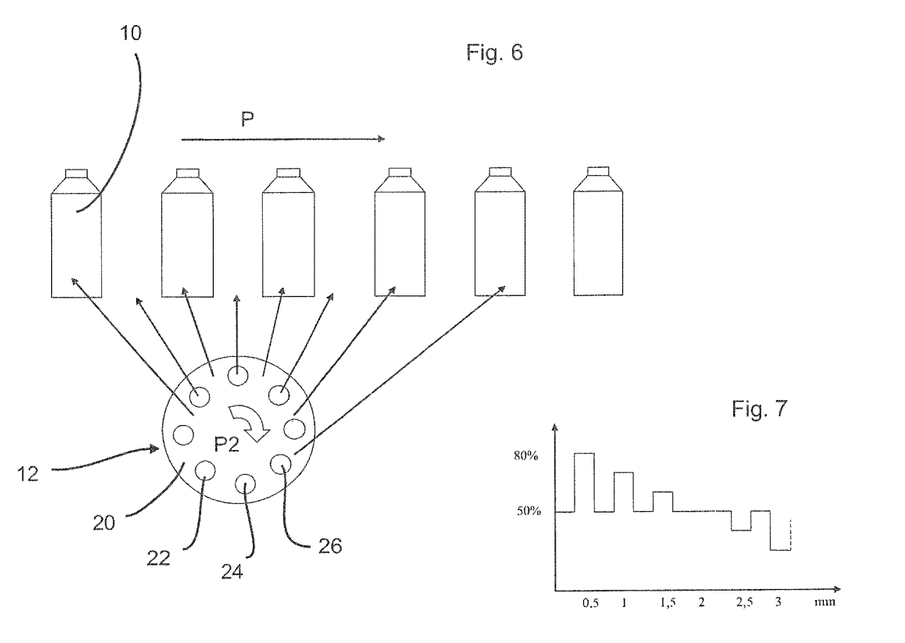
FIG. 6 shows a diagram of one embodiment of a shielding element in the form of a shutter wheel.
FIG. 7 shows a graph of measured values when using a shutter wheel.

FIG. 6 shows a further embodiment of the apparatus according to the invention, wherein the shielding element is configured here as a rotatable element or as a shutter wheel. This shielding element 12 has a carrier 20 which has a certain thickness and brings about a certain shielding of the radiation. Inserted in this carrier is a plurality of windows 22, 24, 26 which each have different thicknesses and thus give rise to different levels of shielding. The containers 10 are moved here in the direction of the arrow P. The shielding element is rotatable, as indicated by the arrow P2.

FIG. 7 shows an example of an intensity curve in the case of different positions of the shielding element shown in FIG. 6. It can be seen that the carrier 20 here gives rise to a shielding or attenuation by 50%. The individual windows 22, 24, 26 cause attenuations differing therefrom, in this case of 80%, 70%, 60%, 40% and 30%. By using such a shielding element 12 in the form of a shutter wheel, it is possible to set or to simulate a number of different shielding effects.

The applicant reserves the right to claim as essential to the invention all the features disclosed in the application documents in so far as they are novel individually or in combination with respect to the prior art.

LIST OF REFERENCES 1 apparatus
2 transport device
4 radiation device
6 sensor device
8 evaluation device
10 containers
12 shielding element
14 movement device
20 carrier
22, 24, 26 window
44 exit window
62 housing
64 opening
66 groove/recess
68 sensor element
82 display device
84 comparison device
P transport path/double-headed arrow
S radiation
R radiation to be detected
P1 direction of movement of the shielding element 12
P2 direction of rotation of the shielding element

The invention claimed is:

1. An apparatus for sterilizing containers, comprising a transport device which transports the containers along a predefined transport path (P), a radiation device which applies radiation (S) to at least some sections of the containers and/or components of the apparatus for sterilization purposes, and a sensor device suitable for detecting x-ray radiation which detects x-ray radiation occurring as a result of the radiation (S) emitted by the radiation device,
   wherein
   the apparatus has a shielding element which attenuates radiation reaching the sensor device in a working mode of the apparatus, and a movement device for moving said shielding element relative to the sensor device.

2. The apparatus according to claim 1,
   wherein
   the movement device is configured in such a way that it can remove the shielding element at least partially from a beam path of the radiation reaching the sensor device.

3. The apparatus according to claim 1,
   wherein
   the radiation device is an electron beam device which emits electron radiation.

4. The apparatus according to claim 1, wherein the shielding element attenuates the radiation impinging on the sensor device by at least 10%.

5. The apparatus according to claim 1, wherein the apparatus has a housing surrounding the sensor device.

6. The apparatus according to claim 1, wherein the shielding element attenuates the radiation impinging on the sensor device by at least 20%.

7. The apparatus according to claim 1, wherein the shielding element attenuates the radiation impinging on the sensor device by at least 30%.

8. The apparatus according to claim 1, wherein the shielding element attenuates the radiation impinging on the sensor device by at least 50%.

9. The apparatus according to claim 1, wherein the shielding element is moveable to cover the sensor or detector element during normal sterilization operation of the apparatus, and is removable for testing purposes.

10. The apparatus according to claim 1, wherein the sensor is adapted to detect only x-rays.

11. The apparatus according to claim 1, wherein the sensor device and the radiation device are arranged in a beam path of the radiation device and on opposite sides of the transport path.

12. The apparatus according to claim 1, wherein the sensor device is arranged outside radiation device.

13. The apparatus according to claim 1, wherein the shielding element is configured as a rotatable element or as a shutter wheel.

14. The apparatus according to claim 1, wherein the shielding element comprises a carrier having a plurality of windows each of which windows provides a different level of shielding.

15. The apparatus according to claim 14, wherein the shielding element is rotatable.

16. The apparatus according to claim 1, wherein the sensor device includes a housing for surrounding sensible electronic components of the sensor device, the housing having an opening or aperture through which x-ray radiation can travel to reach sensor elements of the sensor device.

17. The apparatus according to claim 16, wherein the housing has a groove or recess in which the shielding element is adapted to slide or move.

18. The apparatus according to claim 1, wherein the shielding element is arranged on a lever adapted to move the shielding device in and out of a shielding position.

19. A method for sterilizing containers, wherein the containers are transported along a predefined transport path (P), and wherein the containers or components of an apparatus for sterilizing containers are sterilized at least in some sections by being exposed to radiation, and wherein a sensor device suitable for detecting x-ray radiation detects x-ray radiation occurring as a result of said radiation, wherein a shielding element attenuates radiation reaching the sensor device, and the shielding element is moved at least at times relative to the sensor device such that radiation reaching the sensor device is attenuated to a degree.

20. The method according to claim 19, wherein for the purpose of checking the sensor device, the shielding element is moved relative to the sensor device such that the radiation reaching the sensor device is attenuated to a lesser degree.

21. The method according to claim 19, wherein the radiation device applies charge carriers and in particular electrons to the containers or to components of the apparatus.

* * * * *

UNITED STATES PATENT AND TRADEMARK OFFICE
CERTIFICATE OF CORRECTION

PATENT NO. : 9,474,813 B2  
APPLICATION NO. : 14/647719  
DATED : October 25, 2016  
INVENTOR(S) : Krueger

Page 1 of 1

It is certified that error appears in the above-identified patent and that said Letters Patent is hereby corrected as shown below:

On the Title Page

Item [30], Foreign Application Priority Data, "10 2012 111 494" should read --10 2012 111 494.3--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*